US00PP27283P3

(12) United States Plant Patent
Olesen et al.

(10) Patent No.: US PP27,283 P3
(45) Date of Patent: Oct. 18, 2016

(54) ***CLEMATIS* PLANT NAMED 'EVIPO066'**

(50) Latin Name: *Clematis cartmanii*
Varietal Denomination: Evipo066

(71) Applicants: Mogens Nyegaard Olesen, Fredensborg (DK); Raymond J. Evison, St. Sampsons (GG)

(72) Inventors: Mogens Nyegaard Olesen, Fredensborg (DK); Raymond J. Evison, St. Sampsons (GG)

(73) Assignee: Poulsen Ruser A/S, Fredensborg (DK)

( * ) Notice: Subject to any disclaimer, the term of this patent is extended or adjusted under 35 U.S.C. 154(b) by 132 days.

(21) Appl. No.: 14/121,276

(22) Filed: Aug. 15, 2014

(65) Prior Publication Data

US 2016/0050827 P1 Feb. 18, 2016

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

"Perfection by Poulsen—*Clematis* Main Varieties 2013" (3 pgs total).*
Retrieved from internet on Feb. 16, 2016 for www.poulsenroser.com/assortment/clematiscollections/boulevard/kimiko.aspx (1 pg total).*

* cited by examiner

*Primary Examiner* — Susan McCormick Ewoldt

(57) ABSTRACT

A new *Clematis* plant with a compact growth habit, profuse, white flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

4 Drawing Sheets

Botanical classification: Genus: *Clematis*. Species: *cartmanii*.

Variety denomination: 'Evipo066'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling.

The two parents were crossed during the summer of 1995 and the resulting seeds were planted the following winter in a controlled environment in Guernsey, Channel Islands. The new variety named 'Evipo066' originated as a single seedling from the stated cross.

The new *clematis* plant may be distinguished from its female seed parent and male pollen parent primarily by flower period and flower size. The new variety has larger flowers than the parent varieties. The new variety initiates flower development earlier than the parent varieties.

The objective of the hybridization of this *clematis* plant was to create a new and distinct variety for nursery culture with unique qualities such as:

1. Uniform and abundant white flowers;
2. Vigorous and compact growth, making the variety suitable for container culture; and
3. Early flowering.

This combination of qualities was lacking in *clematis* plants that were in commercial cultivation and the qualities have been substantially achieved in the new variety.

'Evipo066' was selected by Mogens N. Olesen and Raymond J. Evison in their *clematis* development program in the Channel Islands, United Kingdom in 1996. Asexual reproduction of 'Evipo066' by means of vegetative cuttings and traditional layering was first performed by Mogens N. Olesen and Raymond J. Evison in the nursery during the summer of 1996. This initial and subsequent asexual propagations have demonstrated that the characteristics of 'Evipo066' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo066'.

Specifically illustrated in FIG. 1 are tepals detached, reproductive flower parts detached and flower pedicel without petals.

Figure 1:
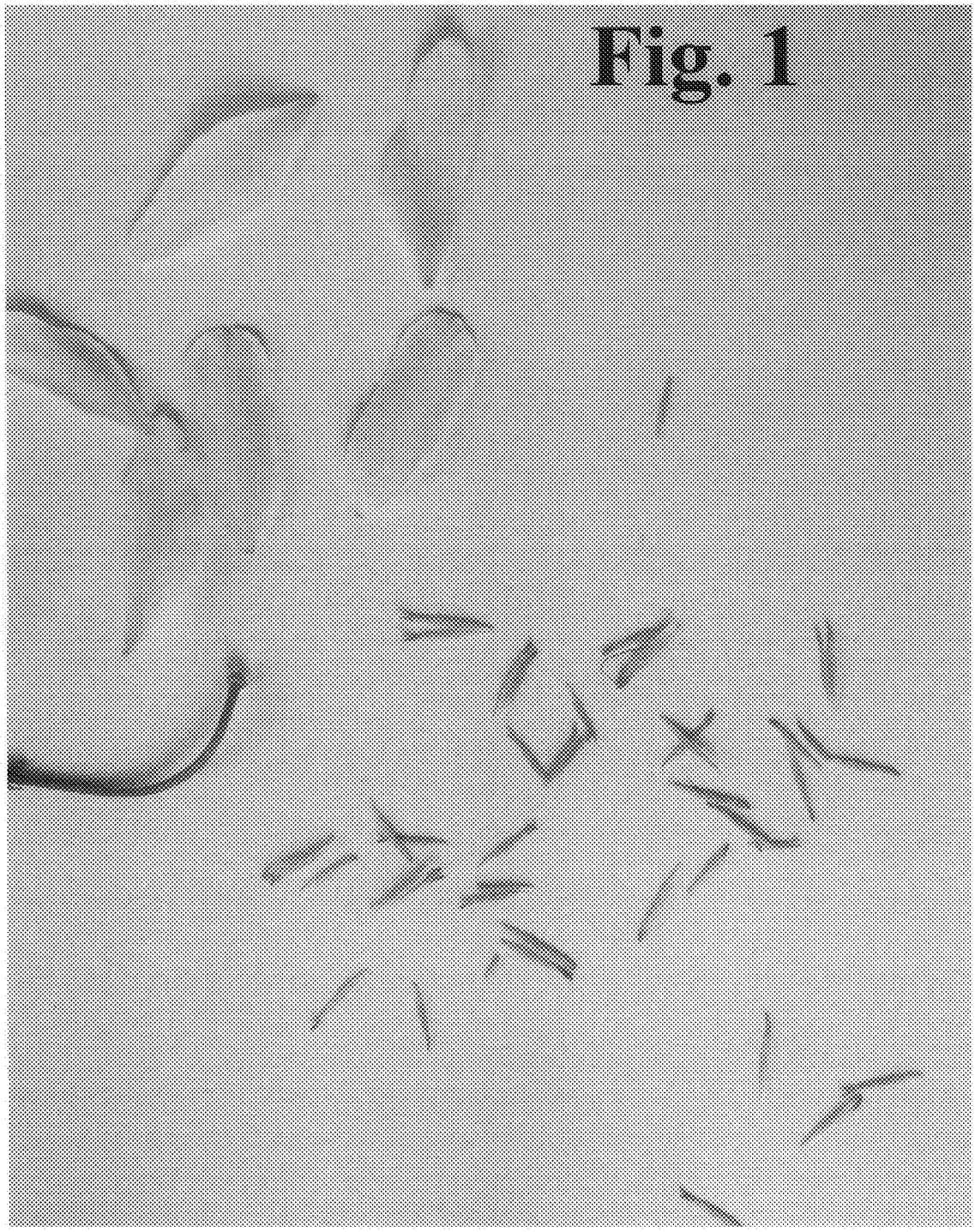
Figure 2:
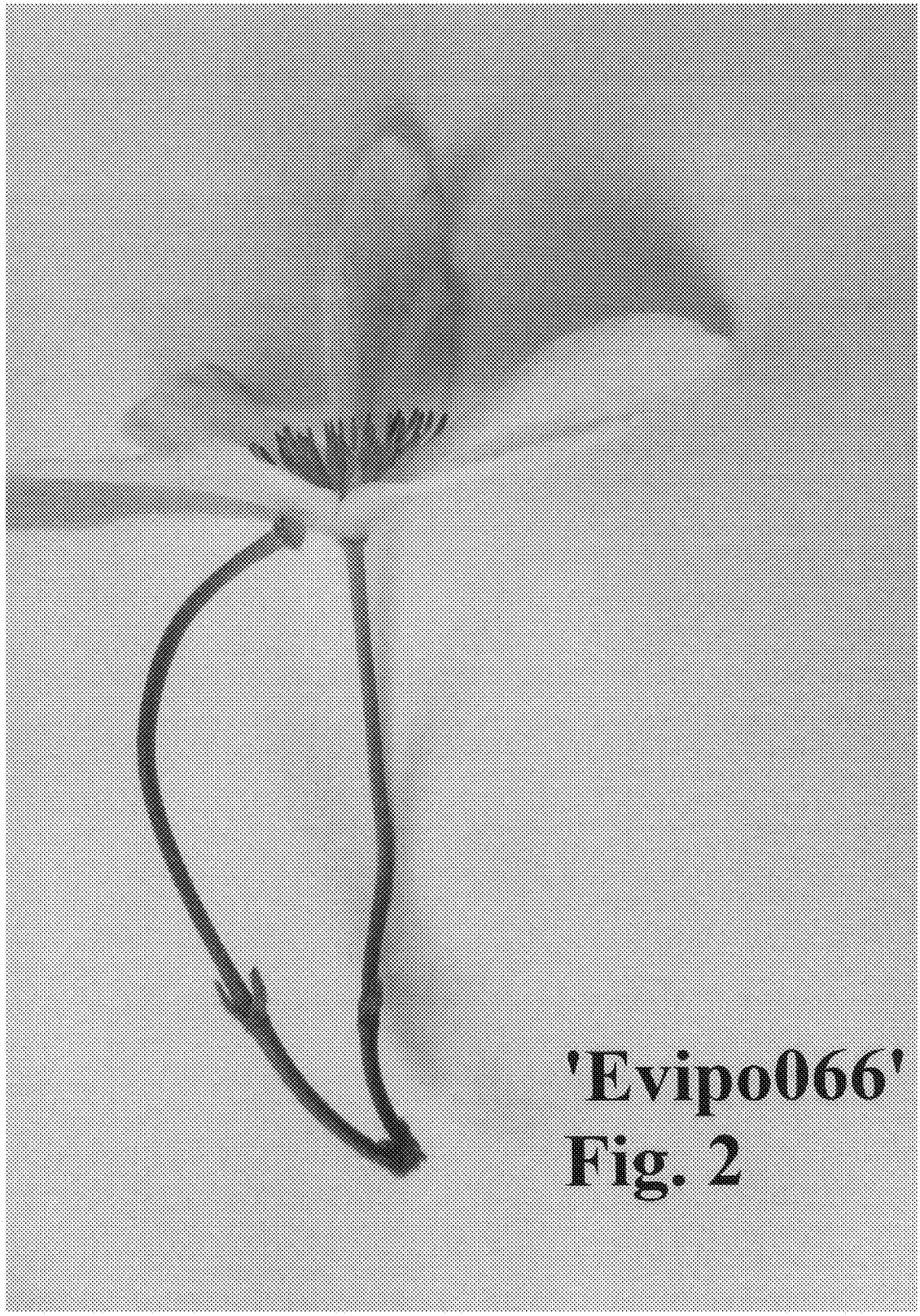
FIG. 2 shows an open flower with pedicel.
Figure 3:
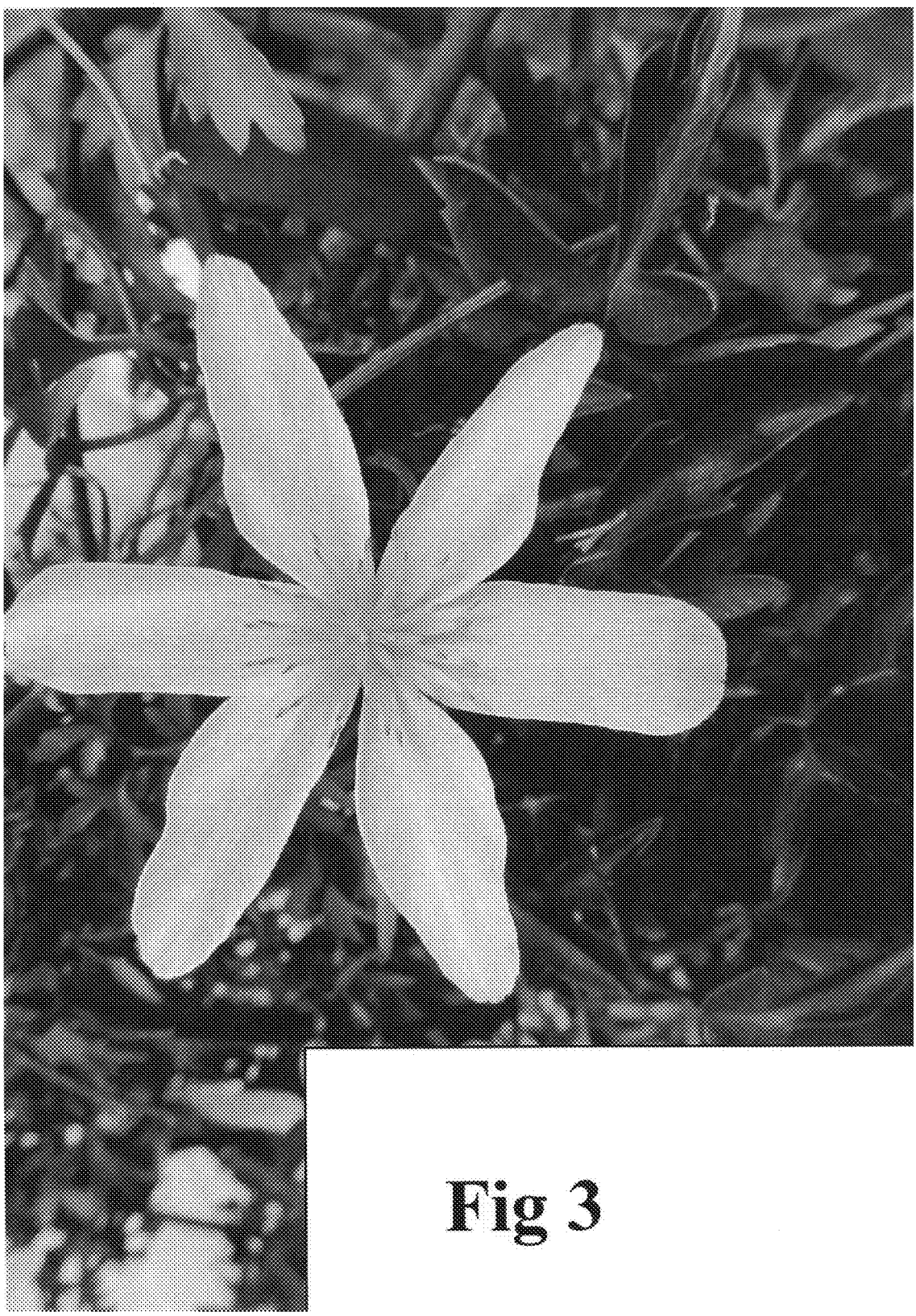
FIG. 3 shows an open flower with foliage and stems in the background.
Figure 4:
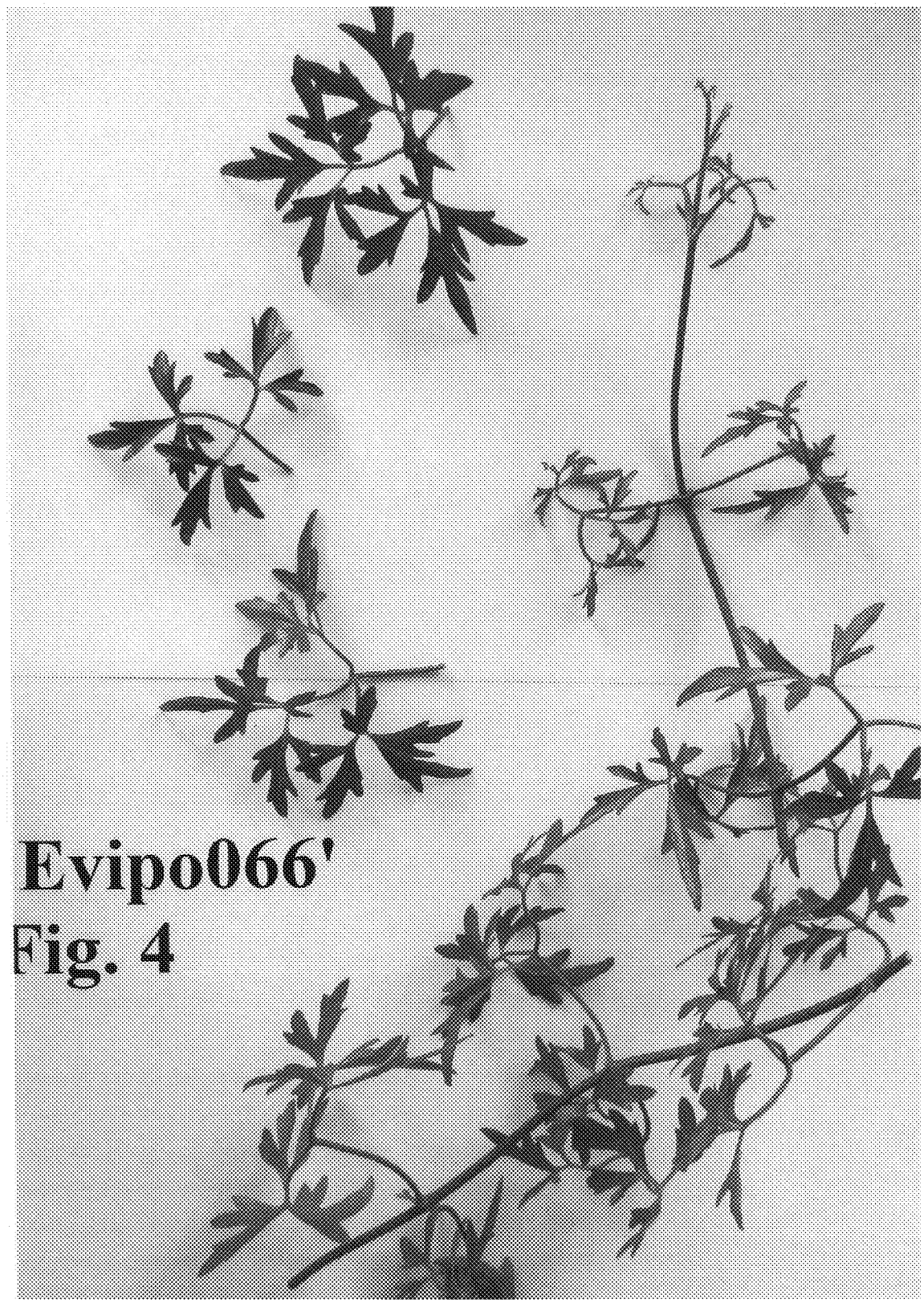
FIG. 4 shows leaves and stems.

Plants shown are 2 years of age.

DETAILED DESCRIPTION OF THE VARIETY

The following is a detailed description of 'Evipo066', as observed in its growth throughout the flowering period in Fredensborg Denmark. Observed plants were cultivated for a period of 2 years in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, physical characteristics of a non-patented *clematis* variety *Clematis×cartmanii* 'Joe' are compared to 'Evipo066' in Chart 1.

CHART 1

| | 'Evipo066' | 'Joe' |
|---|---|---|
| Flower diameter | 60 mm | 35 mm |
| Tepal overlap | none | partial |

Flower and Flower Bud

Blooming habit: The natural flowering period is April to May.

Peduncle:
- *Surface texture*.—Lightly pubescent.
- *Length*.—35-50 mm.
- *Color*.—Yellow-Green Group 146D.
- *Strength*.—Moderately strong.

Receptacle:
- *Surface texture*.—Smooth, lightly pubescent.
- *Shape*.—Funnel.
- *Size*.—2 mm (h)×2 mm (w).
- *Color*.—Yellow-Green Group 146D.

Flower arrangement:
- *Location on vine*.—Old growth.
- *Borne*.—Flowers develop from nodes along the stem.
- *Attitude*.—Upwards.

Flower bloom:
- *Size*.—On average, flowers are 60 mm in diameter and 10 mm in depth.
- *Profile*.—Open flowers are flat.
- *Fragrance*.—None.
- *Lasting quality*.—Flowers normally remain 7 days on the plant.

Tepals:
- *Tepal color*.—The upper surface and lower is Green White Group 157B.
- *Quantity*.—Normally 6 tepals.
- *Size*.—30 mm in length by 10 mm wide.
- *Shape*.—Individual tepal shape is lanceolate. The tepal apex is rounded. The base is acute.
- *Apex recurvature*.—None.
- *Tepal cross section*.—Flat.
- *Margins*.—Entire.
- *Persistence*.—Tepals drop away cleanly.

Reproductive organs:
- *Pollen*.—None observed.
- *Anthers*.—Size: About 2 mm in length. Color: Greyed-Orange Group 165B. Quantity: On average, 35.
- *Filaments*.—Color: Yellow Group 7B. Length: 10 mm.
- *Pistils*.—None observed.

Seed head characteristics: Not observed.

Plant

Plant form: Bushy.

Plant growth: Moderately vigorous.

Size: Seasons growth attains 60 cm in height. Average spread is 40 cm.

Stems:
- *Color*.—Juvenile stems are Brown Group 200C. Mature stems are Brown Group 200A.
- *Internodes*.—On average, 50 to 70 mm between nodes.
- *Length*.—Normally 15 cm from the base of the plant to the flowering portion of the stem.
- *Diameter*.—Normally 2 to 4 mm.
- *Texture*.—Mature stems are generally smooth.

Plant foliage:
- *Leaf characteristics*.—Evergreen.
- *Arrangement*.—Biternate, opposite.
- *Leaf size*.—Compound leaves are normally 50 to 70 mm (l)×60 to 90 mm (w). Leaflets are normally 25 to 35 mm (l)×15 mm (w).
- *Abundance*.—On average 2 leaves per 10 cm of stem.
- *Leaf color*.—Juvenile upper Yellow-Green Group 146A. Juvenile lower Yellow-Green Group 146B. Mature upper Yellow-Green Group 147A. Mature lower Yellow-Green Group 146A.
- *Stipules*.—Absent.
- *Petioles*.—Size: Normally 30 mm in length by 1 to 2 mm diameter. Texture: Smooth. Color: Yellow-Green Group 147A.
- *Petiolule*.—Size: Normally 12 to 20 mm in length by 1 to 2 mm diameter. Texture: Smooth. Color: Yellow-Green Group 147A.
- *Leaflet shape*.—The base is hastate. The apex is aristate.
- *Margin*.—Lobed.
- *Surface*.—The upper and lower surfaces are smooth.
- *Thickness*.—Thick.
- *Glossiness*.—Glossy.

Disease resistance: Subject to any disease that normally attacks the species.

Cold hardiness: Trials to date show the variety is hardy to −10° C.

Heat tolerance: The variety has been found to be suitable for climate conditions found in the American Horticulture Society heat zone 7.

We claim:

1. A new and distinct variety of *clematis* plant named 'Evipo066', substantially as described and illustrated, due to its abundant white flowers, attractive long lasting foliage, compact growth, suitability for production from softwood cuttings in pots, and flowering under glasshouse conditions, which make the variety suitable for distribution in the floral industry.

* * * * *

'Evipo066'